United States Patent
Ehrlich (10) Patent No.: US 9,789,287 B2
(45) Date of Patent: Oct. 17, 2017

(54) HEAD MOUNTED IV HOLDER ASSEMBLY AND METHOD OF USE

(71) Applicant: Kenneth Ehrlich, Borger, TX (US)

(72) Inventor: Kenneth Ehrlich, Borger, TX (US)

( * ) Notice: Subject to any disclaimer, the term of this patent is extended or adjusted under 35 U.S.C. 154(b) by 0 days.

(21) Appl. No.: 14/335,079

(22) Filed: Jul. 18, 2014

(65) Prior Publication Data

US 2016/0015938 A1 Jan. 21, 2016

(51) Int. Cl.
*A61M 25/02* (2006.01)
*A61B 5/0215* (2006.01)
*A61B 5/00* (2006.01)

(52) U.S. Cl.
CPC .......... *A61M 25/02* (2013.01); *A61B 5/0215* (2013.01); *A61B 5/6803* (2013.01); *A61B 5/6814* (2013.01); *A61B 5/6852* (2013.01); *A61M 2025/0206* (2013.01); *A61M 2025/026* (2013.01); *A61M 2025/0213* (2013.01); *A61M 2210/06* (2013.01)

(58) Field of Classification Search
CPC .......... A61M 2025/0206; A61M 25/02; A61M 2025/0213; A61M 2025/022; A61M 2025/0226; A61M 2025/0253; A61M 2210/06
See application file for complete search history.

(56) References Cited

U.S. PATENT DOCUMENTS

| | | | |
|---|---|---|---|
| 4,665,566 A | | 5/1987 | Garrow |
| 5,131,412 A | * | 7/1992 | Rankin ................. A61F 5/3761 128/869 |
| 5,188,101 A | * | 2/1993 | Tumolo ................... 128/207.18 |
| 6,619,288 B2 | | 9/2003 | Demers |
| 7,284,730 B2 | * | 10/2007 | Walsh et al. ................ 248/74.3 |
| 2008/0103456 A1 | * | 5/2008 | Johnson et al. .............. 604/264 |

OTHER PUBLICATIONS

Advertisement "Dale(R) Headband Breathing Circuit Tube Holder" Included as non-patent-literature Received by fax on Mar. 3, 2015 and filed at the USPTO the same date. Original publication date not known.

* cited by examiner

*Primary Examiner* — Bhisma Mehta
*Assistant Examiner* — Nilay Shah
(74) *Attorney, Agent, or Firm* — Shannon L. Warren (57) ABSTRACT

A head mounted catheter holder assembly is disclosed comprising a head mount assembly and an one or more catheter holders. Said one or more catheter holders comprises a first catheter holder. Said one or more catheter holders attach to said head mount assembly. Said head mount assembly releasably attaches to a head of a user. Said one or more catheter holders releasably hold a one or more catheter tubes.

8 Claims, 7 Drawing Sheets

```
                    ┌─800
┌─────────────────────────────────────────┐
│ Attaching a head mount assembly to a one or │
│        more catheter holders             │
│                 802                      │
└─────────────────────────────────────────┘
                    │
                    ▼
┌─────────────────────────────────────────┐
│   Releaseably attaching said head mount  │
│        assembly to a head of a user      │
│                 804                      │
└─────────────────────────────────────────┘
                    │
                    ▼
┌─────────────────────────────────────────┐
│  Releaseably holding a one or more catheter │
│  tubs with said one or more catheter holders │
│                 806                      │
└─────────────────────────────────────────┘
```

HEAD MOUNTED IV HOLDER ASSEMBLY AND METHOD OF USE

CROSS-REFERENCE TO RELATED APPLICATIONS

Not applicable.

STATEMENT REGARDING FEDERALLY SPONSORED RESEARCH OR DEVELOPMENT (IF APPLICABLE)

Not applicable.

REFERENCE TO SEQUENCE LISTING, A TABLE, OR A COMPUTER PROGRAM LISTING COMPACT DISC APPENDIX (IF APPLICABLE)

Not applicable.

BACKGROUND OF THE INVENTION

This disclosure relates generally to a head mounted catheter holder assembly and method of use. None of the known above inventions and patents, taken either singularly or in combination, is seen to describe the instant disclosure as claimed. Accordingly, an improved head mounted catheter holder assembly and method of use would be advantageous.

BRIEF SUMMARY OF THE INVENTION

A head mounted catheter holder assembly and method of use are disclosed herein.

First, a head mounted catheter holder assembly is disclosed. Said head mounted catheter holder assembly comprises a head mount assembly and a one or more catheter holders. Said one or more catheter holders comprises a first catheter holder. Said one or more catheter holders attach to said head mount assembly. Said head mount assembly releasably attaches to a head of a user. Said one or more catheter holders releasably hold a one or more catheter tubes. Said head mount assembly consists of a headband. Said headband fits around said head of said user. Said one or more catheter holders attach to said headband. Said headband comprises a variable circumference while attaching to said head of said user. Said headband comprises a first fastener having a first portion and a second portion. Said headband comprises a strip of rectangular fabric having a width being longer than its height. Said headband comprises a first end, a second end, an outside surface and an inside surface. Said first portion attaches to said headband at said first end on said outside surface. Said second portion attaches to said headband at said second end on said inside surface. Said variable circumference is altered by selectively attaching said first portion to said second portion.

Next, a head mounted catheter holder assembly is disclosed comprising a head mount assembly and an one or more catheter holders. Said one or more catheter holders comprises a first catheter holder. Said one or more catheter holders attach to said head mount assembly. Said head mount assembly releasably attaches to a head of a user. Said one or more catheter holders releasably hold a one or more catheter tubes.

Finally, a method of using a head mounted catheter holder assembly comprising: attaching a head mount assembly to a one or more catheter holders, releasably attaching said head mount assembly to a head of a user, and releasably holding a one or more catheter tubes with said one or more catheter holders.

DETAILED DESCRIPTION OF THE INVENTION

Described herein is a head mounted catheter holder assembly and method of use. The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1A:
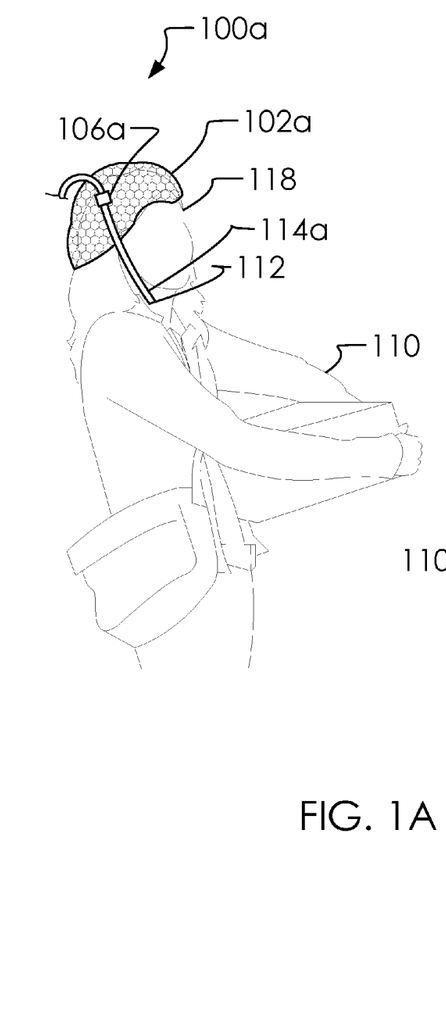
FIGS. 1A and 1B illustrate a perspective overview of a first head mounted catheter holder assembly and a second head mounted catheter holder assembly, respectively.
Figure 1B:
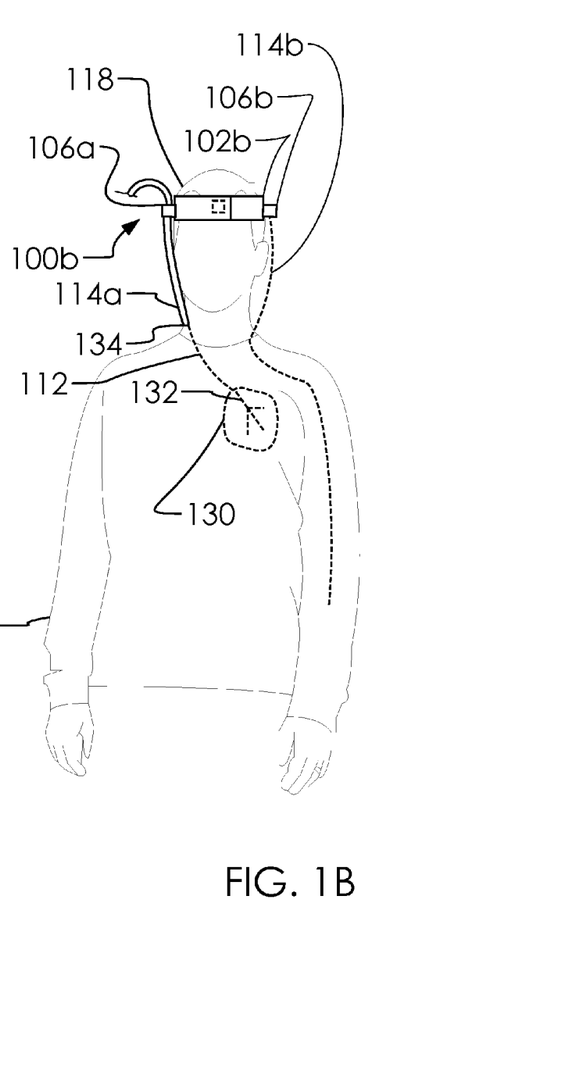

FIGS. 1A and 1B illustrate a perspective overview of a first head mounted catheter holder assembly 100a and a second head mounted catheter holder assembly 100b, respectively.

As illustrated in FIG. 1A, in one embodiment, said first head mounted catheter holder assembly 100a can comprise a first head mount assembly 102a and a one or more catheter holders. In one embodiment, said one or more catheter holders can comprise a first catheter holder 106a. In one embodiment, said first head mount assembly 102a can comprise a snood, a hairnet or similar. In one embodiment, said first head mount assembly 102a can attach to or fit over a head 118 of a user 110. In one embodiment, said one or more catheter holders can hold a portion of a one or more catheter tubes (which can comprise a catheter tube 114*a* and a catheter tube 114*b*). In one embodiment, as is known in the art, said catheter tube 114*a* can attach to a pulmonary artery 112 (or another artery or a vein of a patient) of said user 110.

In one embodiment, said catheter tube 114*a* can pass through one of said one or more catheter holders; wherein, said one or more catheter holders can wrap around said catheter tube 114*a* to secure said catheter tube 114*a* to said first head mount assembly 102*a* or a second head mount assembly 102*b* (as described below).

Now turning to a discussion of FIG. 1B. In one embodiment, said second head mounted catheter holder assembly 100*b* can comprise said second head mount assembly 102*b* and said one or more catheter holders (which can comprise said first catheter holder 106*a* or a second catheter holder 106*b*). In one embodiment, said second head mount assembly 102*b* can comprise a head-band. In one embodiment, said second head mount assembly 102*b* can attach to or fit around said head 118 of said user 110. In one embodiment, said one or more catheter holders can hold a portion of said catheter tube 114*a*.

In one embodiment, as is known in the art, said catheter tube 114*a* can attach to a pulmonary artery 112 of said user 110. In the prior art, said catheter tube 114*a* is often taped to said user 110 in order to prevent rubbing and dislodging from said user 110. A problem arises for users when said catheter tube 114*a* is to be kept in said user 110 for an extended period of time. For example, in the present case, attaching said catheter tube 114*a* to said user 110 with tape allows for the collection of germs on the tape and, ultimately, infection in the pulmonary artery 112. Likewise, the prior art does not secure said catheter tube 114*a* to said user 110 for an extended period of time, as tape loses its adhesiveness over time. Further, tape may cause a restricted movement of air to said user 110's skin. For patients which have facial hair, tape may not adhere to said facial hair. Likewise, often a patient may have sensitive skin which reacts negatively to tape. FIG. 1B further illustrates a heart 130 and a one or more passages 132 within said heart 130.

In one embodiment, said user 110 may need a pulmonary artery catheter 134. In one embodiment, said pulmonary artery catheter 134 can comprise be used for diagnostic purposes. For example, it can detect heart failure or sepsis, monitor therapy, evaluate the effects of drugs and/or deliver drugs to the heart of a user. One advantage of said pulmonary artery catheter 134 can be to direct, simultaneous measurement of pressures in the right atrium, right ventricle, pulmonary artery, and the filling pressure of the left atrium.

As is used in the prior art, taping said catheter tube 114*a* to said user 110 in order to hold said pulmonary artery catheter 134 in place, can lead to dislodging of and infection at said pulmonary artery catheter 134. One advantage of said head mounted catheter holder assembly and method of use, as disclosed herein, is the avoidance of these and other maladies associated with the prior art.

In one embodiment, said first head mounted catheter holder assembly 100*a* and/or said second head mounted catheter holder assembly 100*b* can protect said user 110 by isolating tugs and pulls on said pulmonary artery catheter 134 when said catheter tube 114*a* is moved upstream from said user 110. In one embodiment, said first head mounted catheter holder assembly 100*a* and/or said second head mounted catheter holder assembly 100*b* can be elastic allowing said catheter tube 114*a* to move slightly from said head 118 but not dislodge said pulmonary artery catheter 134 entirely. Said head mounted catheter holder assembly and method of use, therefore, provides protection of said user 110 from harm, infection, and removal of said pulmonary artery catheter 134 (or any catheter) while in use. Further, said insertion point 206 with said first end of said one or more catheter tubes are downstream of said first catheter holder 106*a* and said IV bag 212 and said second end of said one or more catheter tubes are upstream of said first catheter holder 106*a*.

Figure 2A:
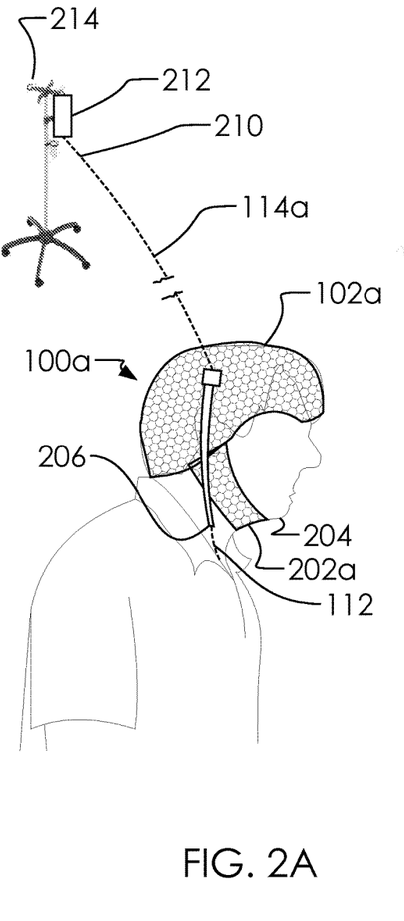
FIGS. 2A and 2B illustrate a perspective overview of said first head mounted catheter holder assembly with a first chin strap and said second head mounted catheter holder assembly with a second chin strap, respectively.
Figure 2B:
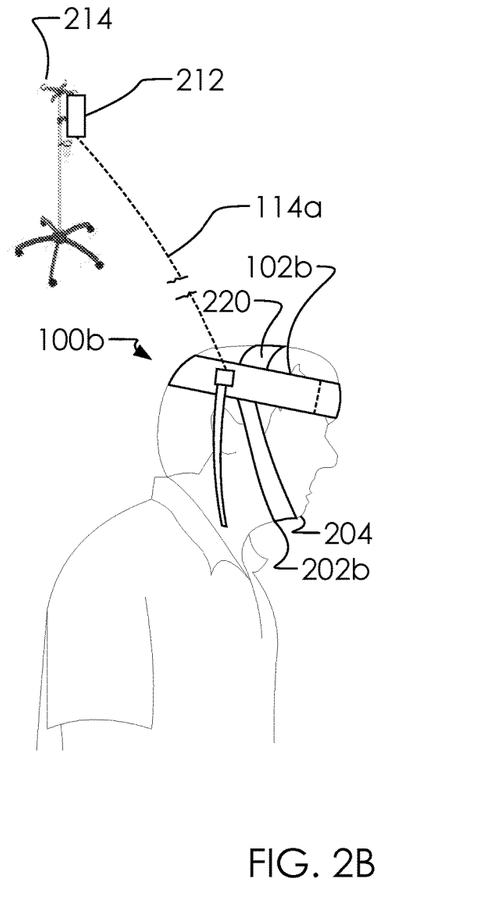

FIGS. 2A and 2B illustrate a perspective overview of said first head mounted catheter holder assembly 100*a* with a first chin strap 202*a* and said second head mounted catheter holder assembly 100*b* with a second chin strap 202*b*, respectively. In one embodiment, said first chin strap 202*a* and said second chin strap 202*b* can be referred to collectively as a chin strap.

In one embodiment, said chin strap 202*a* and/or said chin strap 202*b* can be fastened by a fastener. Said fastener can comprise at least one of a hook and eye, a hook-and-loop fasteners (such as Velcro®), a button and eye, a zipper and fly, and a magnetic attraction.

In one embodiment, said chin strap can wrap around a portion of said head 118 of said user 110. For example, said chin strap can wrap around a chin 204 of said user 110.

In one embodiment, said pulmonary artery catheter 134 is inserted into said user 110 at an insertion point 206, as is known in the art.

In one embodiment, said catheter tube 114*a* can attach to said insertion point 206 at a first end and to an IV bag 212 at a second end. In one embodiment, said IV bag 212 is held by an IV stand 214. As is known in the art, movement of said user 110 can cause said catheter tube 114*a* to put stress on said insertion point 206. One objective of said head mounted catheter holder assembly and method of use is to decrease such stress.

In one embodiment, said second head mounted catheter holder assembly 100*b* can comprise a vertex strap 220, as discussed below.

Figure 3A:
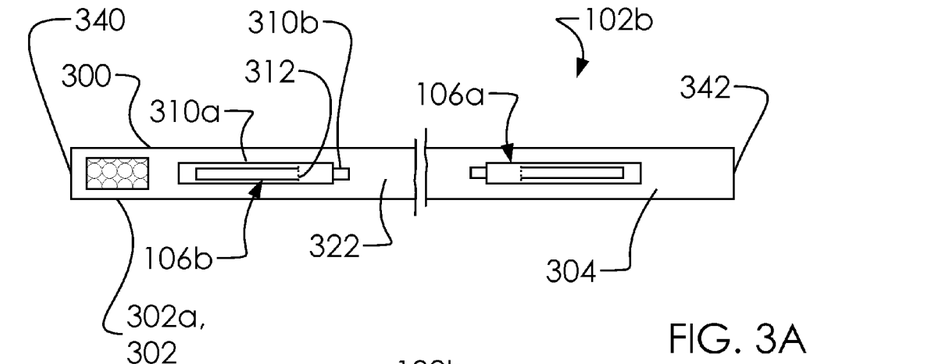
FIGS. 3A, 3B and 3C illustrate an elevated front view, elevated back view, and an elevated bottom view of said second head mount assembly, respectively.
Figure 3B:
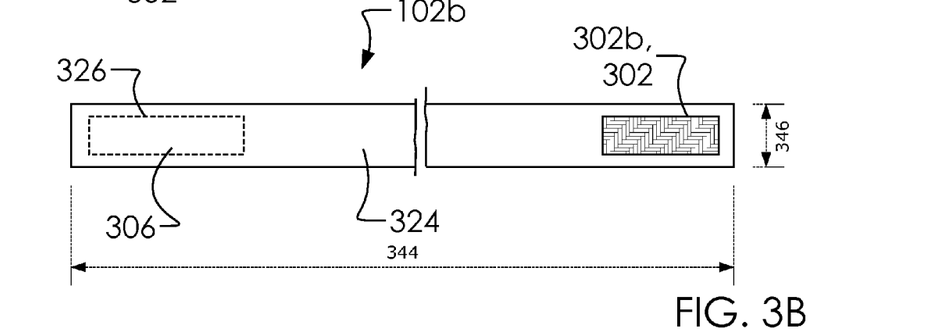
Figure 3C:
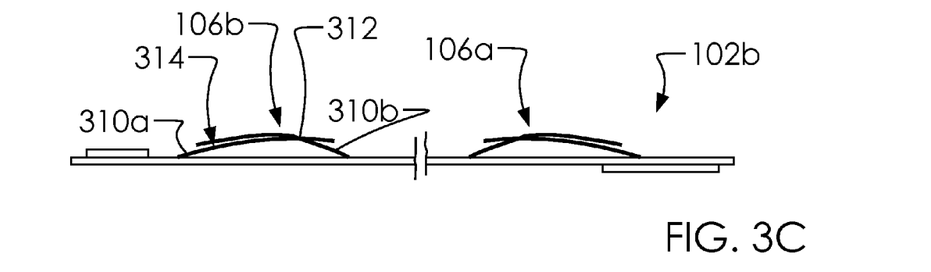

FIGS. 3A, 3B and 3C illustrate an elevated front view, elevated back view, and an elevated bottom view of said second head mount assembly 102*b*, respectively.

In one embodiment, said second head mount assembly 102*b* can comprise a headband 300, a first fastener 302 a first side 304, a second side 306, and said one or more catheter holders. In one embodiment, said first fastener can comprise a hook-and-loop fasteners (having a first portion 302*a* and a second portion 302*b*). In one embodiment, said one or more catheter holders (illustrated here as second catheter holder 106*b*) can comprise a first strap 310*a* and a second strap 310*b*. In one embodiment, said first strap 310*a* can comprise a slit 312; wherein, a portion of said second strap 310*b* can pass through said slit 312. In one embodiment, a portion of said second strap 310*b* can releasably attach to a portion of said first strap 310*a*. In one embodiment, a second fastener 314 can be used to releasably attach said second strap 310*b* to said first strap 310*a*. In one embodiment, said first fastener 302 and said second fastener 314 can comprise at least one of a hook-and-loop fasteners, a hook and eye, a button and eye, a zipper and fly, and a magnetic attraction.

In one embodiment, said second head mount assembly 102*b* can comprise an outside surface 322 (which faces outward relative to said head 118 of said user 110) and an inside surface 324 (which can comprise a portion in contact with said head 118 of said user 110). In one embodiment, a portion of said inside surface 324 is covered with a nonirritant band 326. In one embodiment, said nonirritant band 326 is designed to come into contact with human skin without irritation of said skin. One example of such a material can comprise silicon, felt, microfiber, or other suitable materials, as is known in the art. Accordingly, a first portion of said inside surface 324 comprises said nonirritant band 326 and a second portion (which can be in contact with a portion of a hair of said user 110) does not have a material made to reduce irritation of said skin of said user 110.

In one embodiment, said first fastener 302 comprises a first portion 302a and a second portion 302b. In one embodiment, said first portion 302a attaches to said second portion 302b. In one embodiment, said headband 300 can comprise a first end 340, a second end 342, a width 344 and a height 346. In one embodiment, said first portion 302a attaches to said first end 340 on said outside surface 322; and said second portion 302b attaches to said second end 342 on said inside surface 324. In one embodiment, said width 344 is greater than said height 346. In one embodiment, said inside surface 324 can comprise a substantially rectangular fabric (which can comprise an elastic material). In one embodiment, said headband 300 can comprise a variable circumference; wherein, said variable circumference is set by selectively attaching said first portion 302a to said second portion 302b.

Figures 4A, 4C:
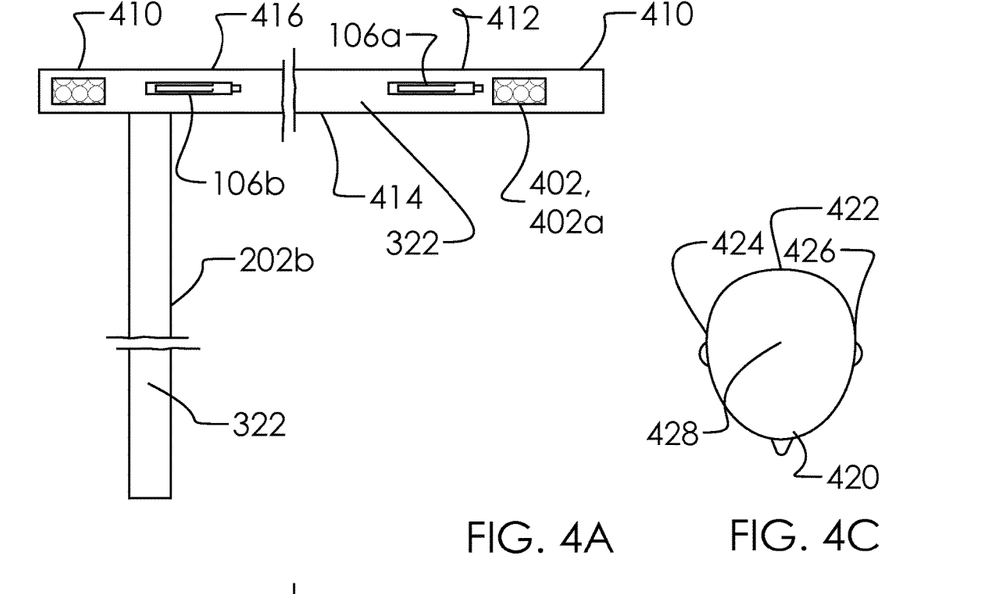
FIGS. 4A, 4B, and 4C illustrate two elevated views and a perspective view, respectively, of said second head mount assembly and an elevated top view of said user.
Figures 4B, 4D:
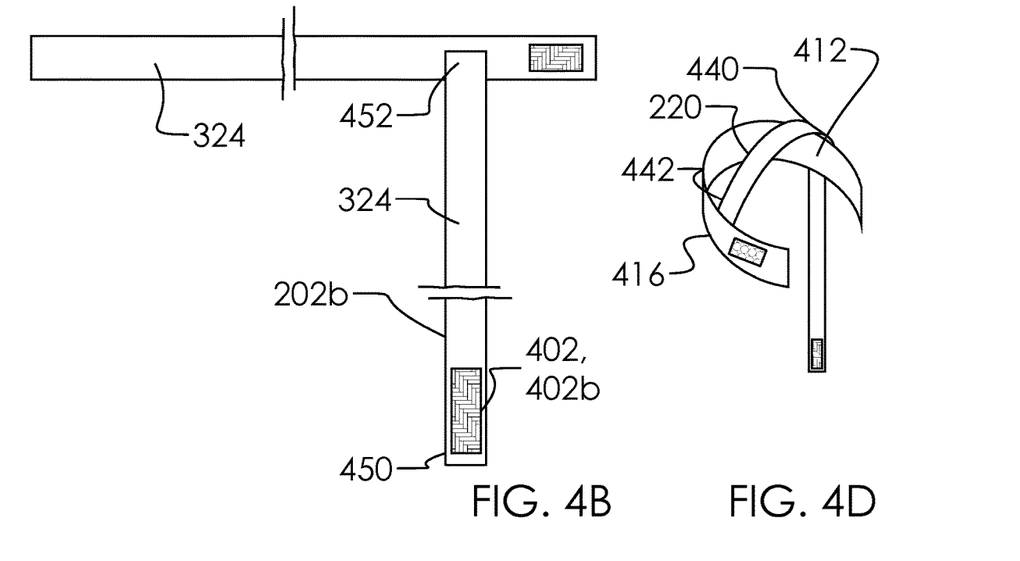
FIG. 4D illustrates a perspective overview of said second head mount assembly with said vertex strap.

FIGS. 4A, 4B, and 4C illustrate two elevated views and a perspective view, respectively, of said second head mount assembly 102b and an elevated top view of said user 110. In one embodiment, said second head mounted catheter holder assembly 100b can wrap around said head 118 of said user 110, wherein; said head 118 of said user 110 comprises a front side 420, a back side 422, a right side 424, a left side 426, and a vertex 428. In one embodiment, said second head mount assembly 102b comprises a front side 410, a first side 412, a second side 416, and a back side 414.

In one embodiment, said second head mounted catheter holder assembly 100b can comprise a fastener 402 (which can comprise a first portion 402a and a second portion 402b) in association with said second chin strap 202b. In one embodiment, said first portion 402a and said second portion 402b are at least one of a hook-and-loop fasteners, a hook and eye, a button and eye, a zipper and fly, and a magnetic attraction. In one embodiment, said first portion 402a can releasably attach to said second portion 402b. In one embodiment, said first portion 402a can be on said first side 412 of said outside surface 322 of said second head mount assembly 102b. In one embodiment, said second portion 402b can be on said inside surface 324 of said second chin strap 202b. In one embodiment, said second chin strap 202b can comprise said outside surface 322 and said inside surface 324 as illustrated and discussed above.

In one embodiment, attaching said second head mounted catheter holder assembly 100b to said user 110 can comprise: wrapping said second head mount assembly 102b around said head 118 of said user 110; attaching said first portion 302a to said second portion 302b; wrapping a portion of said second chin strap 202b around said chin 204 of said user 110; and attaching said first portion 402a to said second portion 402b.

In one embodiment, said fastener 402 attaches at said front side 420 of said head 118 of said user 110. This location has been selected to avoid discomfort at said back side 422 due to thickness of said second head mounted catheter holder assembly 100b and rubbing of a hook-and-loop fasteners at said back side 422.

In one embodiment, said second head mount assembly 102b and said second chin strap 202b can comprise a plurality of apertures (that is aerated) to provide air flow through said second head mounted catheter holder assembly 100b. Although not illustrated as such, this feature would be obvious to one of ordinary skill in the art.

In one embodiment, said front side 410 of said second head mount assembly 102b is aligned along said front side 420 of said head 118. In one embodiment, said second side 416 of said second head mount assembly 102b is aligned along said left side 426 of said head 118. In one embodiment, said first side 412 of said second head mount assembly 102b is aligned along said right side 424 of said head 118. In one embodiment, said back side 414 of said second head mount assembly 102b is aligned along said back side 422 of said head 118 of said user 110. As would be obvious to one in the art, this configuration can be rotated and/or flipped without departing from the intended purpose and scope of this disclosure.

In one embodiment, said first catheter holder 106a attaches to said first side 412 on said outside surface 322; and said second catheter holder 106b attaches to said back side 414 on said outside surface 322.

FIG. 4D illustrates a perspective overview of said second head mount assembly 102b with said vertex strap 220. In one embodiment, said vertex strap 220 can attach over said vertex 428 of said head 118 of said user 110. In one embodiment, said vertex strap 220 can comprise a strap attached between said first side 412 and said second side 416 of said second head mount assembly 102b.

In one embodiment, said vertex strap 220 can comprise a first end 440 and a second end 442. In one embodiment, said first end 440 attaches to said first side 412 and said second end 442 attaches to said second side 416; wherein, said vertex strap 220 extends over said vertex 428 of said head 118 and secures said second head mounted catheter holder assembly 100b to said head 118.

In one embodiment, said second chin strap 202b (otherwise referred to as a "chin strap") can comprise a first end 450 and a second end 452. In one embodiment, said first end 450 attaches to said first side 412 and said second end 452 attaches to said second side 416; wherein, said second chin strap 202b extends around said chin 204 of said head 118 and secures said second head mounted catheter holder assembly 100b to said head 118.

Figure 5A:
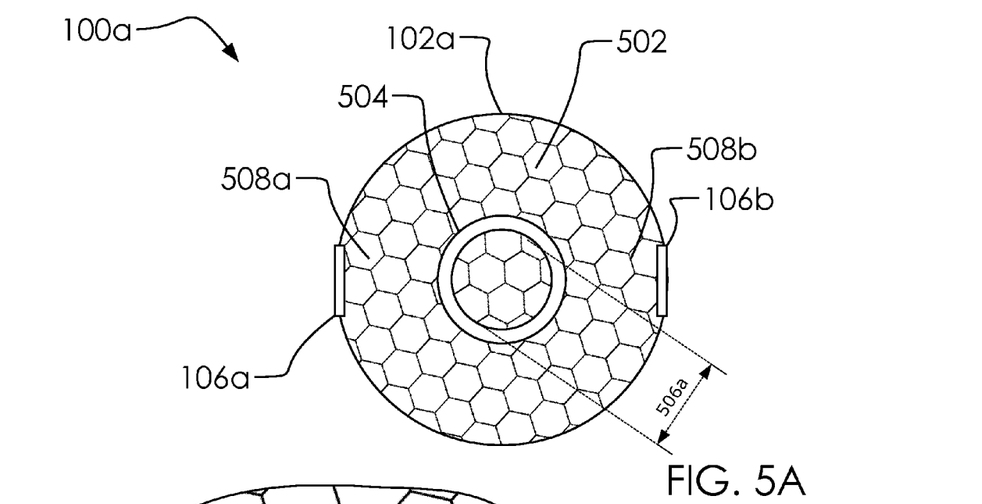
FIGS. 5A and 5B illustrate an elevated front view and an elevated side view of said first head mount assembly.
Figure 5B:
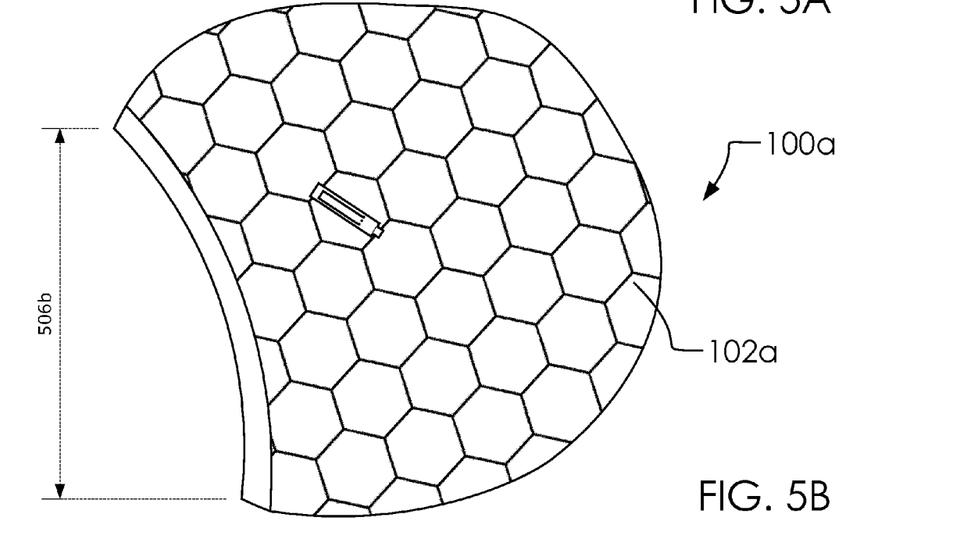

FIGS. 5A and 5B illustrate an elevated front view and an elevated side view of said first head mount assembly 102a. In one embodiment, said first head mount assembly 102a can comprise a mesh portion 502, a fitted rim 504, and a one or more catheter holders.

In one embodiment, said mesh portion 502 can comprise a one of the openings between a one or more threads or cords of a net. In one embodiment, said mesh portion 502 can comprise a snood, which can comprise a type of fashionable head piece used to hold the hair of a user. As is shown in FIG. 1A, a snood can and often is used as a fashion accessory. Here, the use of the term snood, or a hair net, when discussing said mesh portion 502 of said first head mount assembly 102a can be interpreted as a device used to attach to a user's head and hold a weight such as said catheter tube 114a. In one embodiment, said mesh portion 502 can comprise a woven netting or a one or more woven bands, as is known in the art. In one embodiment, said one or more bands can be elastic.

In one embodiment, said mesh portion 502 can comprise a solid fabric, but can also comprise of loosely knitted material (such as a yarn) or other net-like material (hereafter referred to as a netted material). In another embodiment, a small bag—netted, tatted, knitted, crocheted, or knotted—of fine thread, can enclose a bob of long hair on the back of the head or hold it close to the nape.

In one embodiment, said fitted rim 504 can be elastic allowing for a variable circumference and snug fit around said head 118 of said user 110. For example, in one embodiment, said mesh portion 502 is illustrated with a first diameter 506a in FIG. 5A and with a second diameter 506b in FIG. 5B. In another embodiment, said fitted rim 504 can comprise a draw string which allows for a variable circumference, as is known in the art. In one embodiment, said mesh portion 502 can be buttoned or fastened in a variety of manners as would be obvious to one in the art.

In one embodiment, said one or more catheter holders can attach to a side portions which can comprise a first side 508a and a second side 508b of said mesh portion 502 of said first head mount assembly 102a. Said one or more catheter holders of said first head mount assembly 102a can be substantially identical to those of said second head mount assembly 102b.

Figure 6:
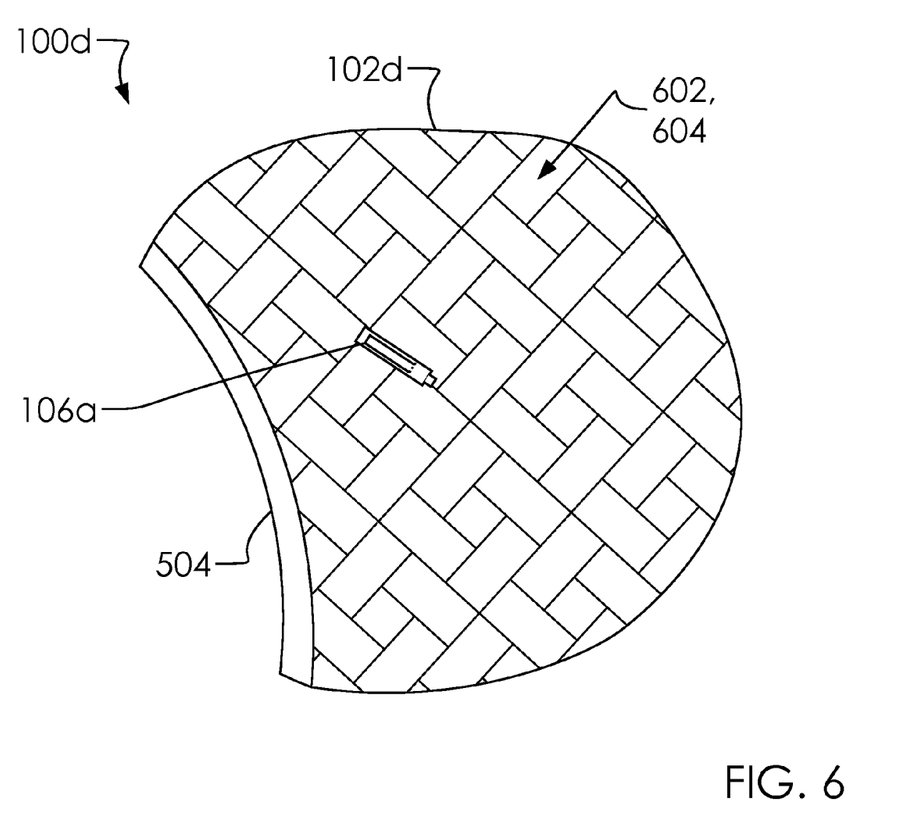
FIG. 6 illustrates an elevated side view of a fourth head mounted catheter holder assembly.

FIG. 6 illustrates an elevated side view of a fourth head mounted catheter holder assembly 100d. In one embodiment, said fourth head mounted catheter holder assembly 100d can comprise a fourth head mount assembly 102d and said fitted rim 504. In one embodiment, said fourth head mount assembly 102d can comprise a woven portion 602. In one embodiment, said woven portion 602 can comprise a plurality of woven strands 604. In one embodiment, said plurality of woven strands 604 can comprise strips of elastic fabric woven to form a hood capable of fitting over said head 118. In one embodiment, said fitted rim 504 stretches around said head 118 and holds said fourth head mounted catheter holder assembly 100d on said head 118.

Figure 7:
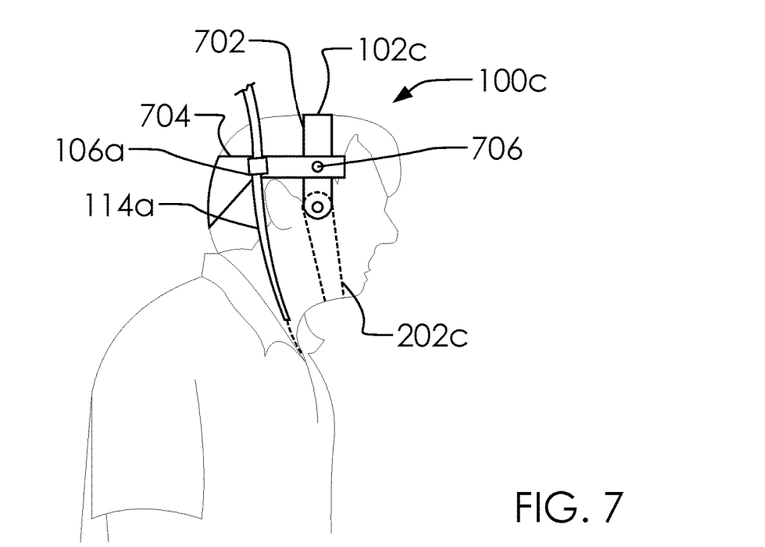
FIG. 7 illustrates an elevated side view of a third head mounted catheter holder assembly.

FIG. 7 illustrates an elevated side view of a third head mounted catheter holder assembly 100c. In one embodiment, said third head mounted catheter holder assembly 100c can function similar to said first head mounted catheter holder assembly 100a and said second head mounted catheter holder assembly 100b, but-for a different version of said first head mount assembly 102a. In one embodiment, said third head mounted catheter holder assembly 100c can comprise a third head mount assembly 102c (having a vertical portion 702 and a horizontal portion 704), and said one or more catheter holders, a third chin strap 202c. In one embodiment, said vertical portion 702 fits over said vertex 428 of said head 118, and said horizontal portion 704 wraps around said back side 422 of said head 118. In one embodiment, said chin strap 202c can be optional. In one embodiment, said vertical portion 702 and said horizontal portion 704 can meet at a hinge 706. In one embodiment, said hinge 706 allows said vertical portion 702 and said horizontal portion 704 to rotate relative to one another. In one embodiment, a second hinge can be used on an opposite side of said third head mounted catheter holder assembly 100c as would be understood in the art.

Figure 8:
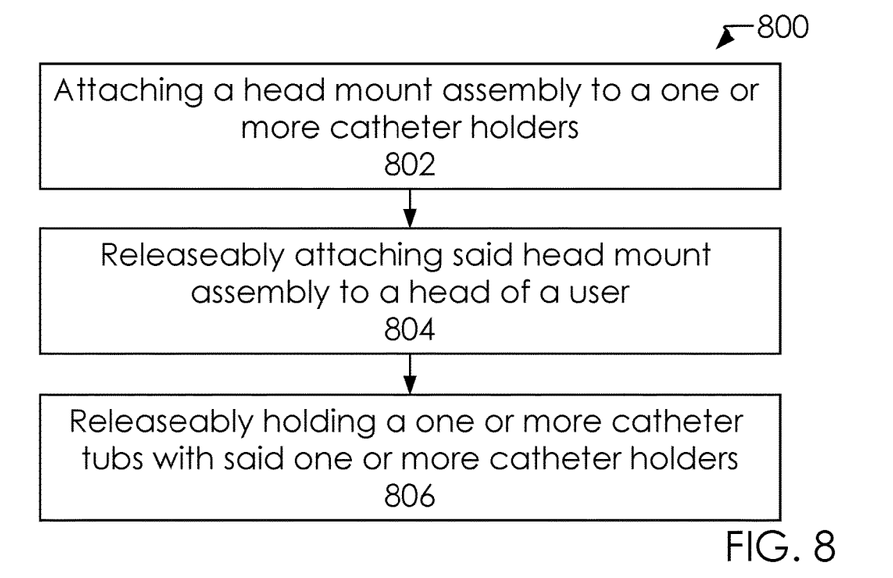
FIG. 8 illustrates a flow diagram of a method of using said head mounted catheter holder assembly and method of use.

FIG. 8 illustrates a flow diagram 800 of a method of using said head mounted catheter holder assembly and method of use. In one embodiment, said flow diagram 800 can comprise a first step 802 (which can comprise attaching a head mount assembly to a one or more catheter holders), a second step 804 (which can comprise releasably attaching said head mount assembly to a head of a user), and a third step 806 (which can comprise releasably holding a one or more catheter tubes with said one or more catheter holders).

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that he above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. A head mounted catheter holder assembly comprising:
a head mount assembly, one or more catheter holders, one or more catheter tubes, and a catheter;
said one or more catheter holders comprises a first catheter holder;
said one or more catheter holders are attached to said head mount assembly;
said head mount assembly is configured to releaseably attach to a head of a user;
said one or more catheter holders releaseably hold said one or more catheter tubes;
said one or more catheter tubes each comprise
said catheter at a first end of said one or more catheter tubes and
an IV bag at a second end of said one or more catheter tubes;
said one or more catheter holders hold said one or more catheter tubes between said first end and said second end;
said catheter is configured to attach to an insertion point on a neck of said user;
said head mounted catheter holder assembly is configured to relieve stress on said insertion point of said user by supporting said one or more catheter tubes between said insertion point and said IV bag;
said insertion point with said first end of said one or more catheter tubes are downstream of said first catheter holder and said IV bag and said second end of said one or more catheter tubes are upstream of said first catheter holder;
said first catheter holder is positioned above said insertion point;
said head mount assembly consists of a headband;
said headband is configured to fit around said head of said user;
said one or more catheter holders attach to said headband;
said headband comprises a nonirritant band configured to limit irritation of skin of said user of said headband;
said headband comprises an elastic material configured to move without becoming dislodged to isolate tugs and pulls on said catheter when said catheter tube is moved upstream of said one or more catheter holders;
said head mount assembly is configured to securely hold a portion of said catheter tube above said insertion point securely enough that tape is not required to hold said catheter in said insertion point;
said one or more catheter holders comprise said first catheter holder and a second catheter holder;
said head mount assembly comprises a first side and a second side;
said first catheter holder attaches to said first side of said head mount assembly; and
said second catheter holder attaches to said second side of said head mount assembly.

2. Said head mounted catheter holder assembly of claim 1 wherein:
- said headband comprises a variable circumference configured to securely attaching said head mounted catheter holder assembly to said head of said user;
- said headband comprises a first fastener having a first portion and a second portion;
- said headband comprises a strip of rectangular fabric having a width being longer than its height;
- said headband comprises a first end, a second end, an outside surface and an inside surface;
- said first portion attaches to said headband at said first end of said headband on said outside surface;
- said second portion attaches to said headband at said second end of said headband on said inside surface; and
- said variable circumference is altered by selectively attaching said first portion to said second portion.

3. Said head mounted catheter holder assembly of claim 1 wherein:
- said headband further comprises a vertex strap;
- said vertex strap comprise a first end and a second end;
- said first end of said vertex strap attaches to a first side of said headband;
- said second end of said vertex strap attaches to a second side of said headband; and
- said vertex strap is configured to wrap over a vertex of said head of said user.

4. Said head mounted catheter holder assembly of claim 1 wherein:
- said headband further comprises a chin strap;
- said chin strap comprise a first end and a second end;
- said first end of said chin strap attaches to a first side of said headband;
- said second end of said chin strap attaches to a second side of said headband; and
- said chin strap is configured to wrap around a chin of said head of said user.

5. Said head mounted catheter holder assembly of claim 1 wherein:
- said one or more catheter tubes are configured to attach to said user with said catheter at said first end of one or more catheter tubes and said IV bag at said second end of said one or more catheter tubes; and
- said catheter comprises a pulmonary artery catheter.

6. Said head mounted catheter holder assembly of claim 1 wherein:
- said headband comprises a mesh material configured to limit skin irritation by stretching and allowing airflow while in use.

7. Said head mounted catheter holder assembly of claim 1 wherein:
- said headband comprises a silicon material configured to limit skin irritation.

8. Said head mounted catheter holder assembly of claim 1 wherein:
- said headband comprises a microfiber material configured to limit skin irritation by stretching and allowing airflow while in use.

* * * * *